(12) United States Patent
Lo

(10) Patent No.: US 7,822,469 B2
(45) Date of Patent: Oct. 26, 2010

(54) ELECTROSTATIC DISCHARGE PROTECTION FOR ANALOG COMPONENT OF WRIST-WORN DEVICE

(75) Inventor: Thomas Ying-Ching Lo, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 262 days.

(21) Appl. No.: 12/139,195

(22) Filed: Jun. 13, 2008

(65) Prior Publication Data

US 2009/0312655 A1  Dec. 17, 2009

(51) Int. Cl.
*A61B 5/04* (2006.01)
(52) U.S. Cl. ...................................... 600/509
(58) Field of Classification Search ........... 200/341; 361/679.01; 368/425; 455/300; 600/300, 600/301, 509, 519
See application file for complete search history.

(56) References Cited

U.S. PATENT DOCUMENTS

| | | | |
|---|---|---|---|
| 4,747,086 A | 5/1988 | Shaw | |
| 5,280,646 A * | 1/1994 | Koyama et al. | 455/300 |
| 5,691,962 A | 11/1997 | Schwartz et al. | |
| 2002/0012291 A1 | 1/2002 | Robinett | |
| 2005/0061646 A1* | 3/2005 | Ferri et al. | 200/341 |
| 2005/0113703 A1* | 5/2005 | Farringdon et al. | 600/509 |
| 2005/0243653 A1 | 11/2005 | Lizzi | |

* cited by examiner

*Primary Examiner*—George Manuel
*Assistant Examiner*—Robert N Wieland
(74) *Attorney, Agent, or Firm*—Vierra Magen Marcus & DeNiro LLP

(57) ABSTRACT

A heart rate monitor with analog and digital input mechanisms is provided with electro static discharge (ESD) protection which protects electrical components within the monitor. The heart rate monitor input mechanisms may include externally exposed sensors comprised of a conducting material, such as metal. The sensors may include push buttons, a dial, and one or more sensors for retrieving a heart rate signal, such as a case back for the monitor device. Internal circuitry such as an integrated circuit (IC) performs operations to provide time, a heart rate, and other information through a display. The ESD protection prevents any voltage discharge accumulating on the externally exposed sensors from reaching the one or more ICs and interrupting or negatively affecting performance of the monitor.

22 Claims, 6 Drawing Sheets

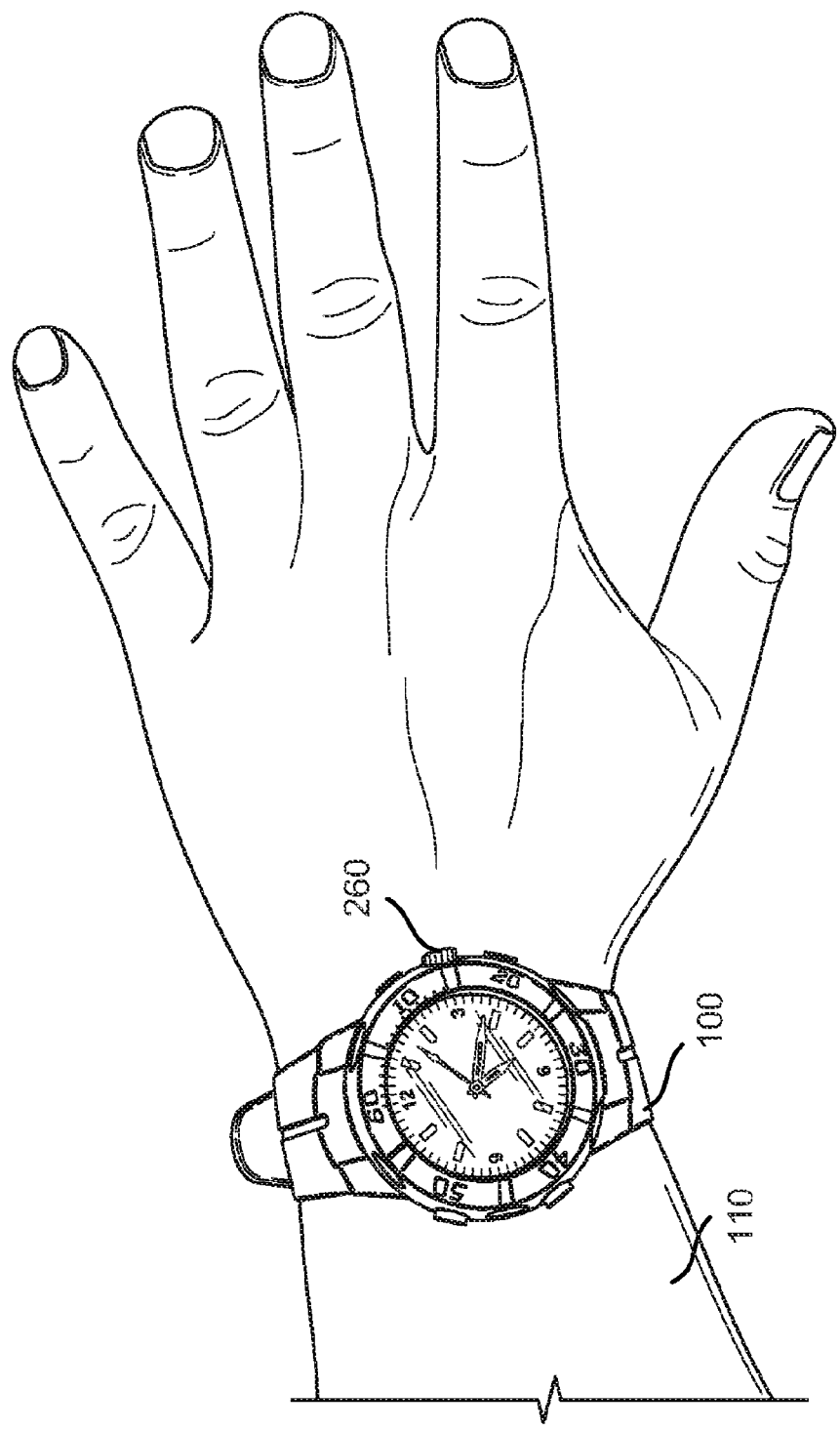

ELECTROSTATIC DISCHARGE PROTECTION FOR ANALOG COMPONENT OF WRIST-WORN DEVICE

BACKGROUND

Wrist worn watches and other devices employ integrated circuits (ICs) to perform various functions while minimizing power usage and size. Though small and efficient, these ICs are susceptible to voltages applied to the circuits as an electro static discharge (ESD). When electro static charge accumulate in a user who wears an electronic device, the high voltage that is created by the static charge may discharge through the integrated circuit or other susceptible portion of the electrical system in the device to a nearby metal object that is at the earth ground potential. By discharging into the circuit, the applied voltage can alter the state of the circuit or cause damage to the circuit. This can be troublesome for wrist worn watches and other devices which have external parts connected to an internal IC or other susceptible circuit.

In most generic analog only or analog/digital wrist watches that have a metal or plastic body, the side push buttons and the crown dial are notoriously vulnerable to electrostatic discharge. The air gap between these parts and the electronic circuits within the watch body presents a relatively low impedance path to high voltages created by static charge. To avoid ESD damage to the electronic circuit, most existing watches employ a metal module clamp mechanically connected to the watch case back. The clamp provides an easy path for EDS discharge current to flow between the case back and the crown dial and between the case back and the side push buttons. For instance, the metal shaft of the crown dial can be physically connected to the module clamp using a spring fastener so that the ESD at the crown dial will go directly to the watch back and not affect any electronic component. The side push button has a controlled air gap by design between it and the clamp. The clamp physically protects the circuitry from the nearby side push buttons when ESD occurs at the push buttons. Therefore, when ESD occurs at the push buttons, the charge will arc through the air gap to the clamp and then to the watch case back. No circuitry will thus be damaged. With this configuration, a static charge won't affect the electronic system.

When a wrist watch has sensors in exposed metal form such as those used for EKG monitoring, body fat and skin temperature measurements and so forth, the ESD protection requires special considerations. The conventional way of connecting the watch module clamp to watch case back directly to bypass ESD can not be applied.

SUMMARY

The present technology, roughly described, provides a heart rate monitor with analog and digital input mechanisms and electro static discharge (ESD) protection to protect electrical components within the monitor. The heart rate monitor may be worn on the wrist and include externally exposed sensors comprised of a conducting material, such as metal. The sensors may include push buttons, a dial, and one or more sensors for retrieving a heart rate signal, such as a case back for the monitor device. Internal circuitry, such as one or more integrated circuits (IC), performs operations to provide time, a heart rate, and other information to a user of the monitor device. The ESD protection prevents any voltage discharge on the externally exposed sensors from reaching the one or more ICs and interrupting or negatively affecting performance of the monitor.

Electro static discharge protection is required to protect monitor circuitry within the monitor from charges that may accumulate on externally exposed portions of the monitor, such as a dial. In typical wrist worn watches having a dial to manipulate analog hour and minute hands in the display, the dial is typically connected to a case back of the watch. This connection allows any discharge occurring at the dial to discharge through the case back of the watch and protect circuitry from an arcing voltage. In some embodiments of the current technology, the case back may be used as a sensor to determine heart rate information. In particular, the case back may be used as one of the EKG sensors to detect electrocardiogram from which heart rate is derived. In this case, a direct connection cannot be made between a dial and the case back because the gearbox, which is mechanically connected and electrically shorted to the dial shaft, would inject electrical noise by the magnetic coil in the gearbox to the heart rate signal received through the EKG sensors, including the case back. Similarly, the ESD protection cannot be altogether eliminated between the dial and the case back or other portion of the monitor as some protection is required to protect the integrated circuitry.

In some embodiments, the ESD protection circuitry implemented between a dial and a watch case back is implemented as a unidirectional component that allows a discharge from the dial to the case back but does not allow noise from the dial to reach the case back. In some embodiments, this ESD protection circuitry is implemented as a transient voltage suppressor diode. The diode may be connected with the anode end to the watch case back and the cathode end to a dial or gearbox incorporating the dial. The diode in this configuration presents a high impedance path for the gearbox noise signal to reach the sensors and thus not interfere with heart rate signals retrieved by the monitor through the sensors.

This summary is provided to introduce a selection of concepts in a simplified form that are further described below in the description. This summary is not intended to identify key features or essential features of the claimed subject matter, nor is it intended to be used as an aid in determining the scope of the claimed subject matter.

BRIEF DESCRIPTION OF THE DRAWINGS

FIG. 1 is an illustration of a wrist worn heart rate monitor worn by a user.

DETAILED DESCRIPTION

Figure 2A:
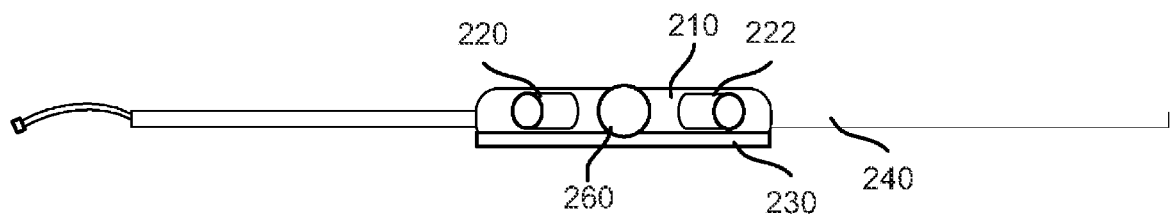
FIG. 2A is an illustration of a side view of a wrist worn heart rate monitor.

A heart rate monitor with analog and digital input mechanisms is provided with electro static discharge (ESD) protection which protects electrical components within the monitor. The heart rate monitor input mechanisms may include externally exposed sensors comprised of a conducting material, such as metal. The sensors may include push buttons, a dial, and one or more sensors for retrieving a heart rate signal, such as a case back for the monitor device. Internal circuitry such as an integrated circuit (IC) performs operations to provide time, a heart rate, and other information through a display. The ESD protection prevents any electro static discharge on the externally exposed sensors from reaching the one or more ICs and interrupting or negatively affecting performance of the monitor.

Electro static discharge protection is required to protect monitor circuitry from charges that may accumulate on externally exposed portions of the monitor, such as a dial. In typical wrist worn watches, a dial is used to adjust analog hour and minute hands in the display and is typically connected to a case back of the watch. This connection allows any voltage discharge occurring at the dial to discharge through the watch case back and protects circuitry from an arcing voltage.

In some embodiments, the ESD protection circuitry may comprise a diode that protects internal circuitry from discharge at a gearbox or external dial. The ESD protection circuitry may be comprised of a diode or other circuitry that allows voltage to be discharged through a watch case back. In some embodiments, the ESD protection circuitry may also prevent noise radiated from the gearbox to reach input sensors of the heart rate monitor device. For example, implementing an ESD protection diode or other ESD protection circuitry between a dial with gearbox and a case back sensor may help discharge electrostatic discharge from the dial to the case back as well as reduce noise generated from the dial and/or gearbox from reaching the sensor.

Throughout this discussion, certain parts or modules may be described with reference to a particular device, such as for example a "watch" case back portion. Labeling a case back as a "watch case back" is for exemplary purposes only, and is not intended to limit the implementation of the present technology or suggest any limiting context associated with these portions, such as that associated with a watch. For example, a case back labeled a "watch case back" may be used within a heart rate monitor discussed herein.

In some embodiments of the current technology, the case back may be used as a sensor to determine heart rate information. In particular, the case back may be used as one of the EKG sensors to detect electrocardiogram from which heart rate is derived. In this case, a direct connection cannot be made between a dial and the case back because the gearbox with a built-in magnetic coil which is mechanically connected and electrically shorted to the dial shaft would introduce electrical noise within the heart rate signal received through the EKG sensors such as the case back. Similarly, the ESD protection cannot be altogether eliminated between the dial and the case back or other portion of the monitor as some protection is required to protect the integrated circuitry.

In some embodiments, the ESD protection circuitry implemented between a dial and a watch case back is implemented with a unidirectional component that allows a discharge from the dial to the case back but does not allow noise from the dial to reach the case back. In some embodiments, this ESD protection circuitry is implemented as a transient voltage suppressor diode. The diode may be connected with the anode end to the watch case back and the cathode end to a dial or gearbox incorporating the dial. The diode in this configuration presents a high impedance path for the gearbox noise signal to reach the sensors and thus not interfere with heart rate signals retrieved by the monitor through the sensors.

The voltage suppression circuitry, or voltage discharge circuitry, may be implemented in a heart rate monitor configured in one of several ways. For example, typical sports watches do not have externally exposed metal portions except the case back, which is typically not used as a sensor that connects to the internal circuitry, and a clamp is used to maintain the position of a battery and a display unit with respect to the circuitry of the watch. To manufacture the watch, the manufacturer will usually use a clamp that holds the module from bottom up. In this configuration, the positive end of the battery will be facing down (towards the case back and away from a display on the top of the watch) so that when the watch back is opened, it is easy to replace the battery. When a battery positive terminal is electrically and mechanically connected to the clamp, the microcontroller has to be wired for a pull-down configuration. The simplest way to provide ESD protection in typical sports watches is to connect the clamp to the case back directly. There is no need to provide any discharge circuitry, and to do so would not be economical. For the EKG heart rate monitor of the present technology, both bottom-up or top-down clamps are possible, as well as pull-up or pull-down heart rate monitor circuit configurations.

FIG. 1 is an illustration of a heart rate monitor 100 worn on the wrist of a user 110. The watch includes a display, dial 260, internal circuitry and other components. Dial 260 may be used to set the current time indicated by the analog hands in the display of the watch or the digital display of the watch.

When worn by a user, the case back of the watch may be used as a sensor to detect signal data associated with the user. In some embodiments, the case back can be used to detect a user biometric such as the temperature of the user. It can also be used as one of the electrodes to pick up EKG signals.

FIG. 2A is an illustration of a side view of a wrist worn heart rate monitor. The heart rate monitor of FIG. 2A includes watch case 210, push-buttons 220 and 222, crown dial 260, watch case back 230 and a heart rate monitor band 240. Watch case 210 contains the internal components of the heart rate monitor, such as for example circuitry, one or more clamps to keep the internal components together, plastic housing pieces and other system components. Push-buttons 220-222 allow the user to provide input to circuitry of the watch. In particular, the user may depress one or more buttons inward towards the watch case. The push-buttons and case back may also be implemented as sensing devices which detect a user's heart rate, body fat or some other user biometric. They can also be implemented as mode activating mechanisms to set time, chronograph, alarms, and so forth.

Dial 260 may be manipulated to provide input to the heart rate monitor. In some embodiments, the dial may be pressed in, pulled out, rotated, or a combination of these. In response to the input from the dial, the analog and/or digital components of the device display may change. For example, rotating the dial may move an hour and minute hand in the display of the watch or cycle through modes of the watch. Pressing the dial may cause a function to start or stop, or cycle between different device functions. Additionally, in some embodiments, the dial can be used as one of the heart rate sensors.

Watch case back 230 is attached to the back of the heart rate monitor and may be in contact with a surface of a user. In some embodiments, watch case back 230 may be a sensing device in addition to encasing the monitor components. For example, the case back may be used to transmit and receive signals to and from a user to determine body temperature, heart rate, body fat or some other user biometric.

Figure 2B:
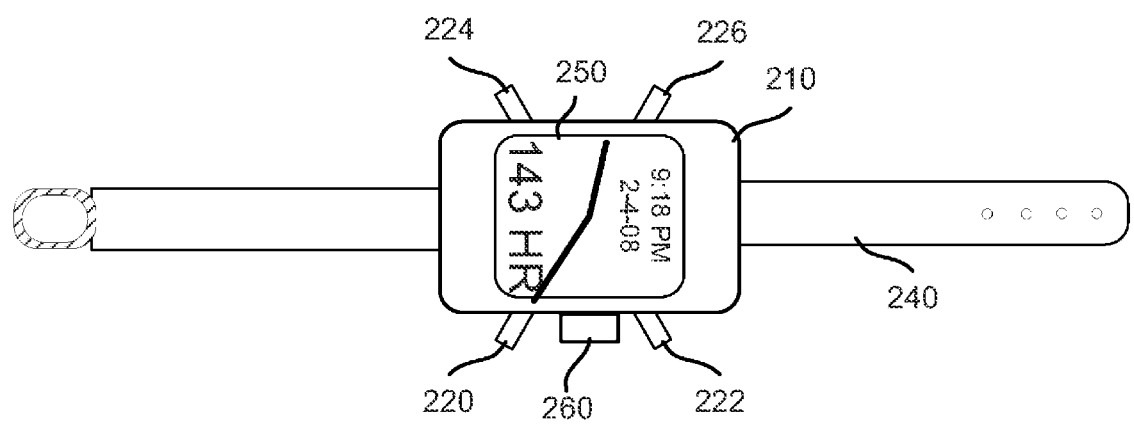
FIG. 2B is an illustration of a top view of a wrist worn heart rate monitor.

FIG. 2B is an illustration of a top view of a wrist worn heart rate monitor. The heart rate monitor of FIG. 2B includes heart rate monitor case 210, push-buttons 220, 222, 224 and 226, dial 260, heart rate monitor band 245 and display portion 250. Push-buttons 220-222, heart rate monitor case 210, dial 260 and monitor band 240 of FIG. 2B are the same as those discussed above with respect to FIG. 2A. Buttons 224 and 226 may be depressed towards case monitor case 210 to invoke a mode selection input such as switching between date, time, stopwatch, and so on, or invoke some other action or state provided by the monitor device. For instance, a heart rate monitor system can use buttons 222 and 224 as sensors. When both are depressed at the same time, a heart rate mode can be activated. In response to activating a heart rate mode, a user's EKG signal can be sensed by 222, 224 and 230 as a regular 3-lead EKG monitor and the heart rate reading can be shown on 250.

Display portion 250 displays information as determined by circuitry within the monitor regarding the current time, date, heart rate of the user, and/or other information. The display portion may include digital display components and analog display components. The digital display component in FIG. 2B is illustrated as indicating that the current time is "9:18 PM," the date is "2-4-08" and a heart rate of "143" has been detected. The analog display component in FIG. 2B is illustrated with an hour hand and minute hand indicating an approximate time of 9:18.

Figure 3:
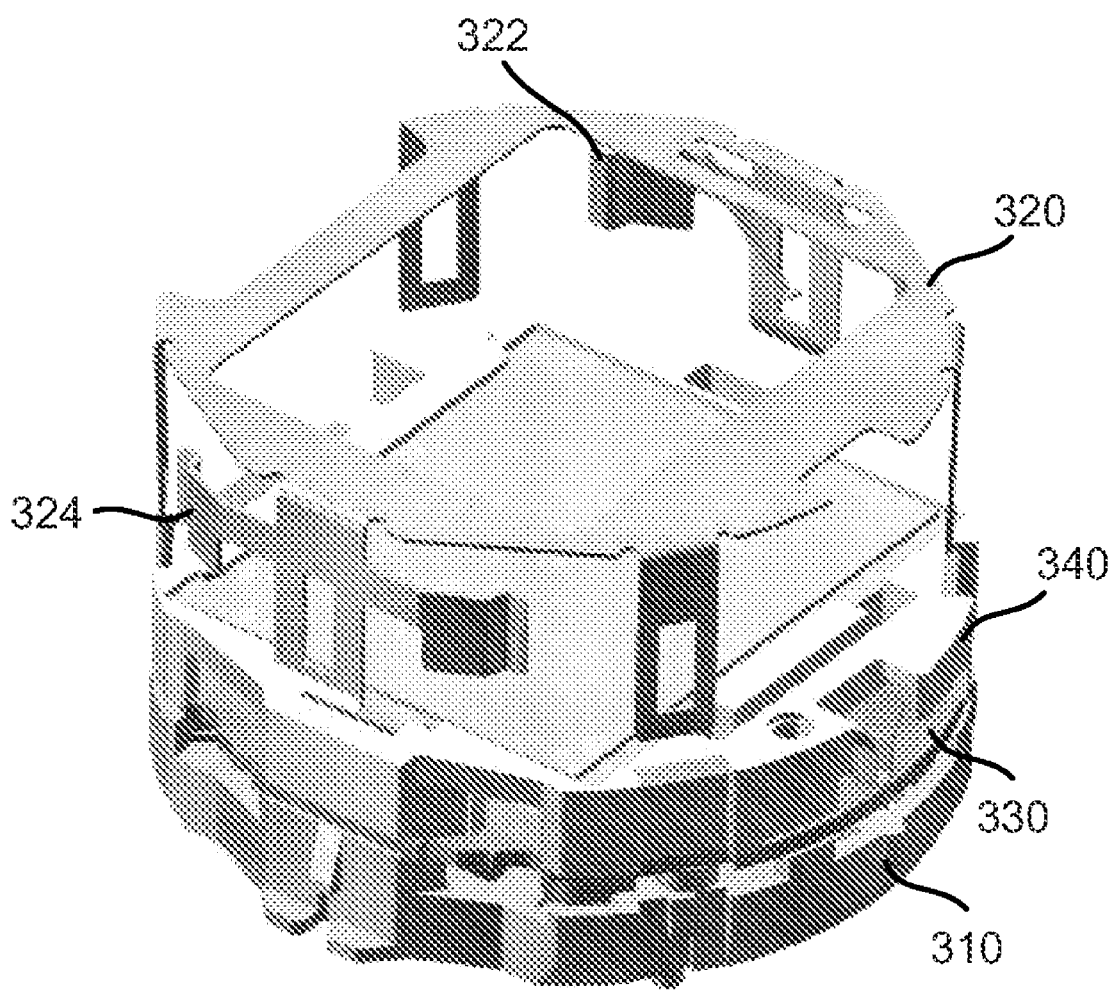
FIG. 3 is an illustration of a module clamp attached to watch circuitry.
Figure 4:
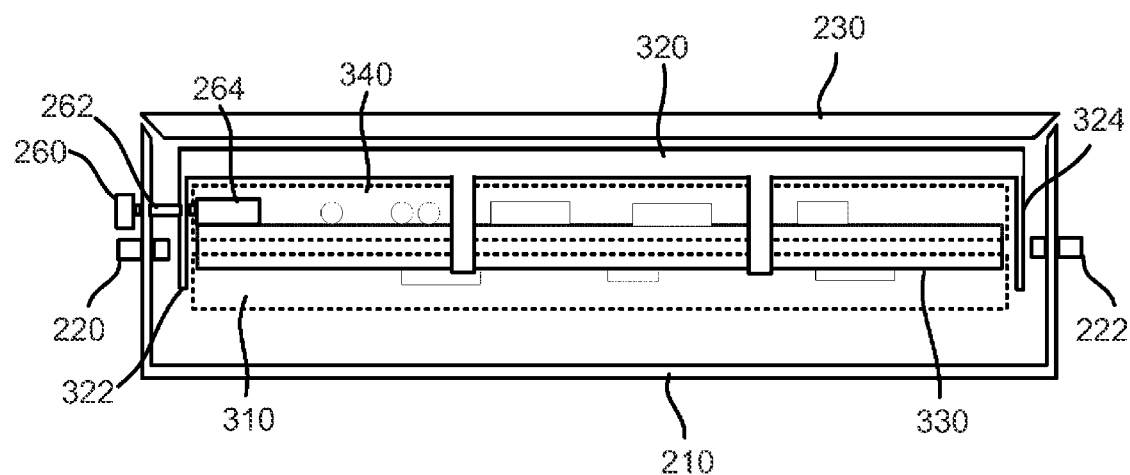
FIG. 4 is an illustration of a cutaway side view of a heart rate monitor.

Within a typical watch, a clamp may be used to secure a battery to the watch circuit. A wrist worn heart rate monitor may also use a clamp mechanism to secure the battery to monitor circuitry. FIGS. 3 and 4 provide illustrations of possible configurations of wrist worn heart rate monitor cases, monitor case back, push buttons and other monitor components.

A heart rate monitor implementing the present technology may have one or more side push buttons and/or one or more watch top buttons. Both side push buttons and watch top buttons may be used as a sensor, such as for example a temperature sensor, electrocardiogram sensor, or some other type of sensor, as well as for providing other input by closing a switch. Though only side push buttons are illustrated in FIGS. 1 and 2A-B, it is intended that any implementation of a heart rate monitor may include a watch top or side push button sensor.

FIG. 3 is an illustration of a module clamp attached to watch circuitry and includes module clamp 320, plastic housing 310 and 340 and heart rate monitor circuitry 330. Plastic housing 310 and 340 have molded cavities to accommodate an opto-electric display such as LCD, LED and/or a battery. For example, the housings can be used to encase and hold in place heart rate monitor circuit 330. The clamp is illustrated as being removed and positioned directly above the monitor circuitry, implementing a top-down configuration. In another embodiment, the clamp can be positioned directly under the monitor circuit (in a bottom up configuration) as depicted in FIG. 4. As illustrated in FIG. 3, module clamp 320 is used to fasten plastic housings 310 and 340 and the heart rate monitor circuit 330 together into a module. The clamp has one or more extensions, such as for example extensions 322 and 324, which are positioned near an edge of the circuit 330. The edge of the circuit between the top and the bottom surfaces of circuit board 330 can be implemented as an electrical contact and plated with gold near extensions 322 and 324. When a push button is pressed, the push button makes contact with an extension which in turn makes contact with the gold plated surface of the circuit edge. Thus, each clamp extension may be viewed as a portion of a switch which closes a circuit when a push button is sufficiently depressed by a user to make contact with the gold plated edge of the circuit, thereby invoking a state change in the circuitry. Operation of heart rat monitor circuitry is discussed with respect to FIGS. 5 and 6 below.

FIG. 4 is an illustration of a cutaway side view of a heart rate monitor. The heart rate monitor of FIG. 4 includes heart rate monitor case 210, push-buttons 220 and 222, heart rate monitor case back 230, dial 260, dial shaft 262, dial gearbox 264, module clamp 320, clamp extensions 322 and 324, plastic housing 310 and 340 and heart rate monitoring circuit 330. Plastic housing portions 310 and 340 are illustrated with dotted lines to indicate that they encompass portions of circuitry 330.

As illustrated, case back 230 is positioned against heart rate monitor case 210 and push-buttons 220-222 may be configured to extend through the monitor case. When depressed, push-buttons 220 and 222 initially make contact with clamp module extension 322 and 324, respectively. When a button is sufficiently depressed, the button displaces a clamp module extension until the extension makes contact with a corresponding portion of circuit 330, such as for example a side edge of the circuit that is gold plated. When contact is made between an extension displaced by a push button and the circuit, the contact closes a circuit switch within the circuit. Circuit operation with switches closed by depressing a push button is discussed below with respect to FIG. 5.

Dial 260 extends externally from monitor case 210 and is connected to gearbox 264 via dial shaft 262. Though not illustrated, ESD protection may be used to protect circuitry within the monitor device from accumulated charges at gearbox 264 and dial 260.

For wrist worn devices, such as a wrist worn heart monitor-watch device, ESD protection may be achieved by isolating outer portions of the device from circuitry which can be damaged by transient voltage discharges or electro-static discharges. With more advanced wrist worn electronic devices that contain external components such as vital sign sensors connected to internal device circuitry, outer portions of the device are often exposed to electrostatic discharge and thus make the internal circuit they connect to vulnerable to damage from the discharges. These advanced devices require protection not provided in typical wrist worn devices.

Figure 5:
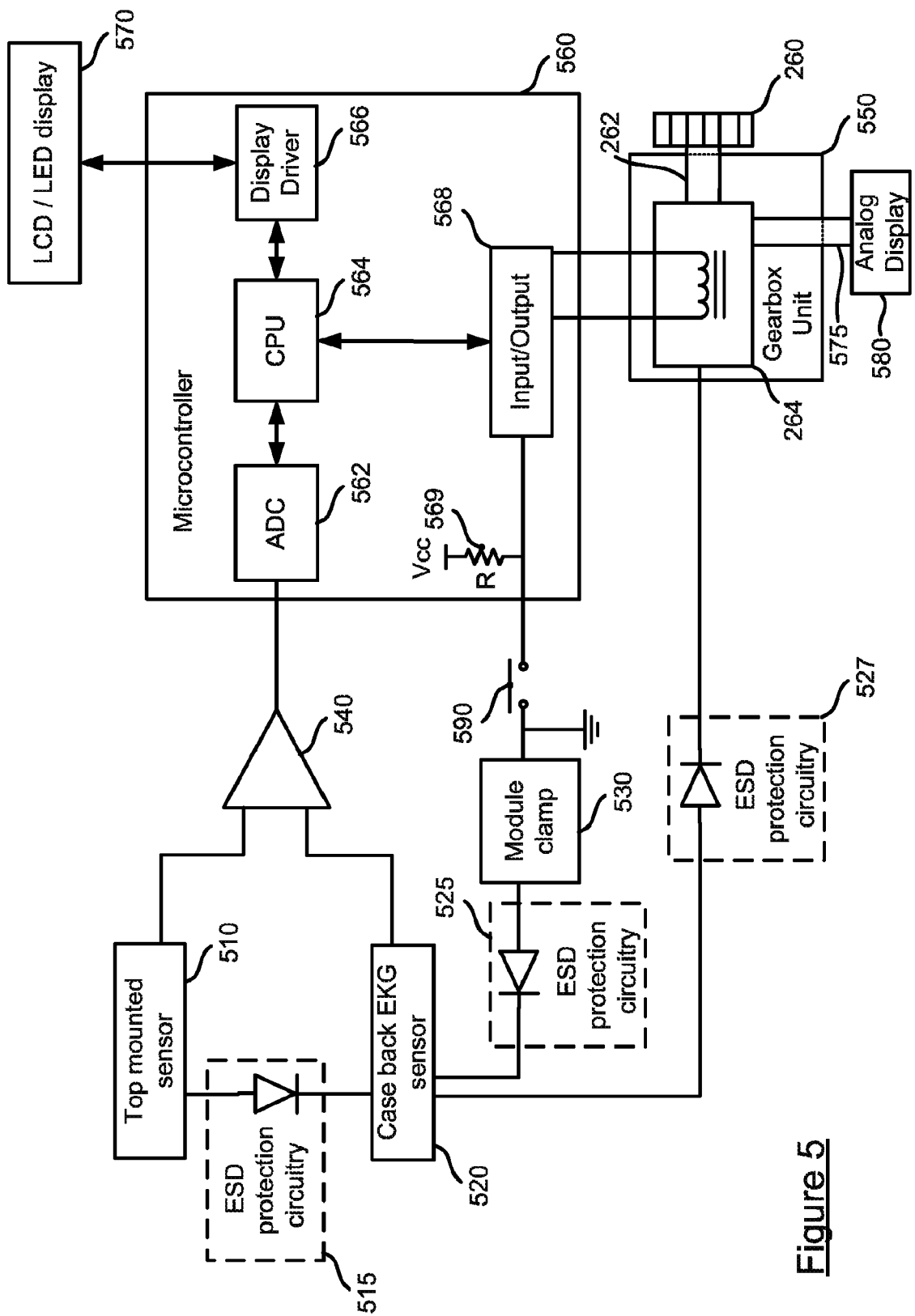
FIG. 5 is a block diagram of an embodiment of a heart rate monitor with voltage discharge circuitry.

FIG. 5 is a block diagram of an embodiment of a system for monitoring a heart rate circuit and providing ESD protection to circuitry components. The ESD protection uses a diode to protect internal circuitry from ESD and prevent gearbox noise radiated by a coil to reach input sensors. The system of FIG. 5 includes watch top mounted EKG sensor 510, case back EKG sensor 520, module clamp 530, amplifier 540, gearbox unit 550, micro controller 560, LCD/LED display 570, and analog display 580. The sensors are described as EKG sensors, each sensor may also be used to detect or measure other user biometrics, including but not limited to temperature.

Watch top EKG sensor 510 is connected to one input of amplifier 540. Case back sensor 520 is connected to another input of amplifier 540. ESD protection circuitry 515 is connected between watch top EKG sensor 510 and case back EKG sensor 520. The output of amplifier 540 is connected to an input of micro controller 560.

Case back EKG sensor 520 is also connected to ESD protection circuitry 525 and ESD protection circuitry 527. The other end of the ESD protection circuitry 525 is connected to module clamp 530 while the other end of ESD protection circuitry 527 is connected to gearbox unit 550. In one embodiment, the cathode side of 527 is connected to gearbox 550 and the anode side is connected to watch case back 520.

Module clamp 530 is connected to circuit ground and to switch actuator 590. Switch actuator may be implanted as a watch top or side push button sensor or switch device. When the switch actuator 590 is closed, a connection is made between module clamp 530 and micro controller 560. The switch actuator represents the actual gold plated edge surface of the circuitry 330 in FIGS. 3 and 4. In some embodiments, a heart rate monitor of the present technology may be implemented with any number of push buttons which are represented as "switch actuators" in FIG. 5, including one push button corresponding to switch actuator 590, two, three, more or no push buttons.

Gearbox unit 550 is connected to ESD protection circuitry 527 and micro controller 560. Gearbox unit 550 includes dial 260, dial shaft 262, and gearbox 264 and is connected to analog display 580 through analog display shaft 575. As a user manipulates dial 260, the analog display shaft 575 may be engaged to change analog display 580. For example, as the dial 260 is adjusted clockwise, hour and minute hands on a display of the monitor may be rotated in a clockwise manner. Additionally, a signal may be received by gearbox 550 from micro controller 560. In some embodiments, the analog display may be connected to gearbox 264 with one or more gears rather than using shaft 575.

Micro controller 560 includes analog to digital conversion module 562, central processing unit 564, display driver 566, input/output module 568 and a pull-up resistor 569. The analog to digital conversion module 562 receives the output of amplifier 540. The signal output from amplifier 540 is converted to a digital signal and provided to central processing unit 564. Central processing unit 564 receives the digitized amplified signal, receives a signal from input/output module 568 and determines a heart rate from the information received. The heart rate signal or other heart rate information is provided to display driver 566 which then provides the heart rate information to a user through display 570. Input/output module 568 outputs signals to drive gearbox to move the second hand or other hands or portions in the analog display. Module 568 also receives input signals from switch actuator 590. As discussed above, switch actuator 590 represents any side push button, of which there may be one, two, three or some other number incorporated within a heart rate monitor system.

ESD protection circuitry 527 provides ESD protection for gearbox unit 550 with respect to micro controller 560. In particular, if a voltage charge accumulates on dial 260 or somewhere else within gearbox unit 550, the voltage may be discharged through ESD protection circuitry 527 to case back sensor 520. This allows the voltage to be reduced and directed away from circuitry 560. Additionally, ESD protection circuitry is provided between the case back sensor 520 and watch top EKG sensor 510 and module clamp 530. Each instance of ESD protection circuitry may be implemented as a diode or some other circuitry. For example, ESD protection circuitry 527 may be implemented as an ESD diode with the cathode connected to gearbox unit 550 and the anode connected to case back EKG sensor 520. Some of the reasons and advantages for particular configurations of an ESD protection diode as part of ESD protection circuitry 527 are discussed in the following paragraphs.

A crown dial, or dial, within a heart rate monitor device is usually comprised of metal and mechanically connected by a metal shaft to the body of a gearbox, which is also usually made of metal. The gearbox typically includes an inductor coil which is energized by electronic pulses provided by rotating the dial. The energized coil causes a stepper motor to advance one step per pulse or per second. The body of the gearbox is electrically isolated from the coil and the rest of the electronic system.

When the case back of the monitor is used also as a biometric sensor, the case back becomes part of the electronic system and can no longer be connected to the gearbox directly. Otherwise, the radiated noise from the coil in the gearbox may propagate to the case back and other portions of the electronic system through the user's fingers when the user touches and manipulates the dial while wearing the watch on the wrist. The body impedance is relatively low and provides a path for the noise to travel from the coil to the dial and eventually to the case back in the form of a differential signal. The differential noise signal will be amplified at the same time as the EKG signal and thus degrades the signal-to-noise-ratio and compromises the accuracy of the measurement.

As discussed above, disconnecting the gearbox body from the case back eliminates the differential noise injection but causes other problems. The gearbox is isolated from the electronic system and any noise generated by the gearbox becomes a common mode noise when the gearbox is not connected to the case back. Common mode noise can be easily removed by using a differential amplifier with adequate CMMR (common mode rejection ratio). However, without connecting the gearbox to any other part of the circuitry, the device loses ESD protection with respect to voltages that may accumulate in the dial or gearbox.

The technology herein uses a low leakage ESD protection diode between the gearbox assembly and the case back of the monitoring device with cathode and anode properly connected as mentioned before. In this way, the leakage in the diode will not compromise the common mode rejection capability of the following differential amplifier but will provide adequate ESD protection to the dial. The low leakage diode ensures isolation between the gearbox and case back but can quickly pass any static charge from the dial to case back or vice versa to protect the watch.

If the ESD protection diode in the ESD protection circuitry is unidirectional, then its anode is tied to case back to ensure electrical isolation from gearbox, as illustrated in FIG. 5. This diode can be any fast Zener diode, Schottky diode or Transient Voltage Suppressor diode, or other suitable diodes. A partial list of examples of suitable diodes includes a Comchip TV06B100JB-G Bi-directional single diode, On Semi DF6A6.8FUT1G Uni-directional TVS Array diode and NUP4102XV6 Bi-directional TVS Array diode, Comchip CEBS065V0-G Bi-directional TVS Array diode, Samtech RCLAMP0521P Bi-directional TVS single diode and SMF3.3 Uni-directional TVS Array diode, and Vishay SMF5V0A Uni-directional TVS single diode, VESD05C-FC1 Bi-directional TVS single diode and VESD05A5a-HS3 Uni-directional TVS array diode.

The operation of the circuit of FIG. 5 is as follows. When a push button or actuator 590 is depressed, for instance, heart rate mode is activated by microcontroller 560. An EKG signal is picked up by sensors 510 and 520 and is amplified by differential amplifier 540. Microcontroller 560 receives the amplified signal, converts the amplified analog signal to digital format and processes the signal to determine heart rate information, such as the heart rate associated with the differential EKG signal. The heart rate information is then displayed through display 570.

When a transient voltage accumulates at gearbox 550 or dial 260, the charge may dissipate over ESD protection circuitry 527 and be channeled to watch case back sensor 520. By placing the ESD protection circuitry between gearbox 550 and case back sensor 520, the microcontroller (and other circuitry within the monitor) is protected from unwanted electro-static discharge and transient voltage discharges.

Figure 6:
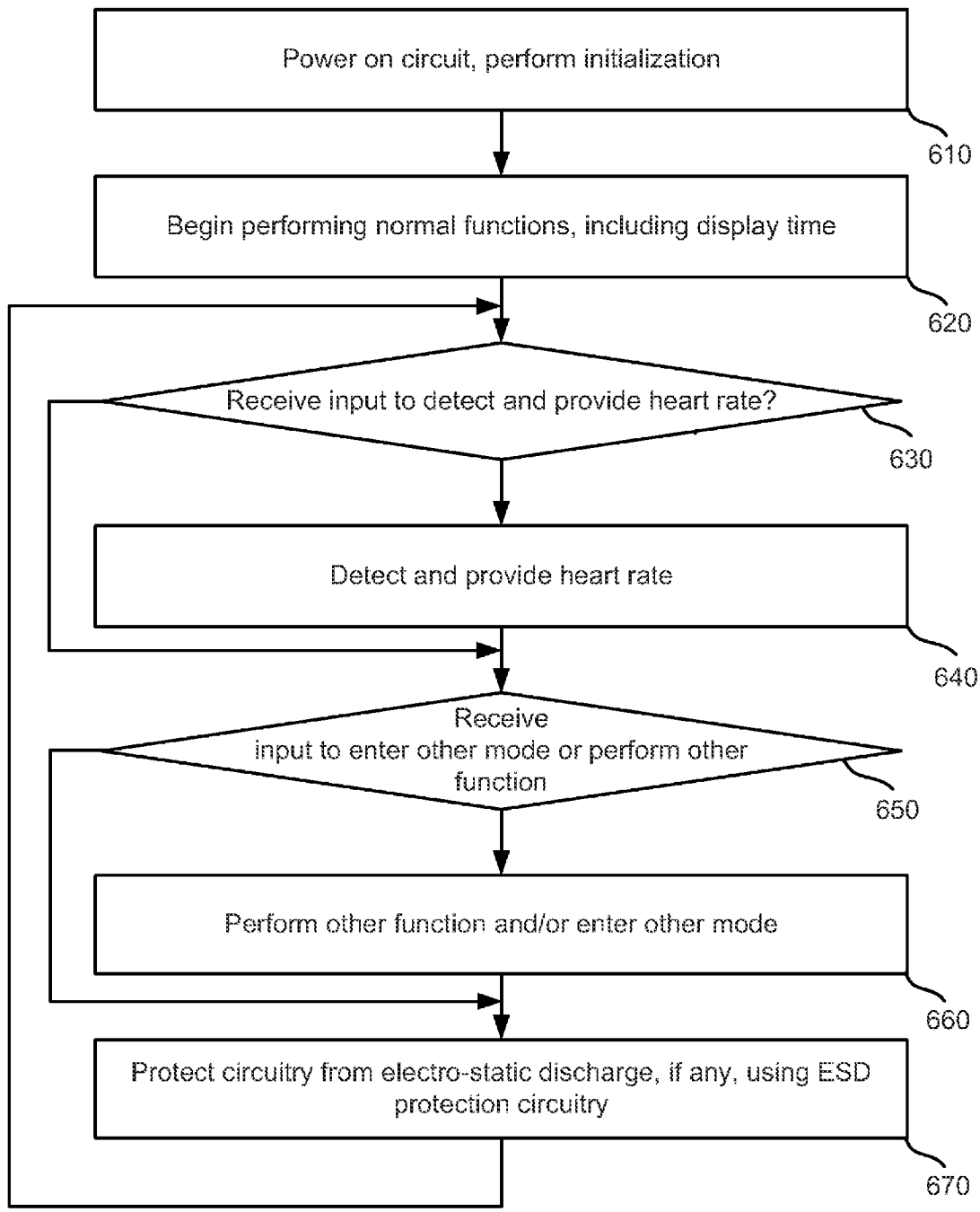
FIG. 6 is a flow chart of an embodiment of a method for protecting circuitry from electro static discharges.

FIG. 6 is a flow chart of an embodiment of a method for protecting circuitry from electro static discharge. First, the heart rate monitor circuit is powered on and an initialization is performed at step 610. For example, the circuit may be powered on by inserting a battery. An initialization may include determining that the battery has an appropriate level to operate the circuit and determine the current time. In some embodiments, power on and initialization may be performed from a sleep mode state.

The heart rate monitor then starts to perform normal functions including the display of time at step 620. The date may also be displayed as an initial function at step 620.

A determination is made as to whether input is received to detect and provide a heart rate for a user at step 630. The input may be a selection of one or more push-buttons 220 or some other mechanism on the watch. If input is received to detect and provide a heart rate, the heart rate is detected and provided at step 640. Detecting and providing a heart rate may require retrieving a pulse signal, determining the pulse component of the signal and determining the heart rate from the pulse component. Detecting and providing a heart rate is discussed in more detail in U.S. Pat. No. 5,876,350, filed on Nov. 7, 1996, having inventors Thomas Ying-Ching Lo and Yuh Show Tsai, all of which are incorporated herein.

A determination is then made as to whether input is received to enter another mode or perform another function at step 650. The other mode or function input may be received as selection of a push-button 220 or some other input mechanism of the heart rate monitor. If input is not received at step 650, the method of FIG. 6 continues to step 670. If input is received, the other function and/or other mode is entered at step 660 in response to receiving the input.

At any time during the operation of the method of FIG. 6, circuitry within the heart rate monitor, including microcontroller 560, is protected from electro static discharge, transient voltage, or any other related voltage damage at step 670. The protection is implemented using voltage discharge circuitry components within the heart rate monitor, such as ESD protection circuitry 527, 525 and 515. When an electro static voltage charge accumulates, the voltage may discharge through the voltage discharge circuitry (VDC). The VDC may be any circuitry that protects the important watch circuitry from ESD damage by bypassing the electrostatic charge from the circuitry. For example, an electrostatic discharge at dial 260 may be protected by allowing the discharge to travel to watch case back EKG sensor 520 through ESD protection circuitry 527. From the watch case back EKG sensor 520, the discharge flows to the user and effectively to ground. In some embodiments, the voltage discharge circuitry may be implemented as a diode. Step 670 may be performed at any time during the operation of FIG. 6 including after power on, before power on or any other time.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

I claim:

1. A wrist-worn device, comprising:
   a monitor case;
   a display connected to the monitor case at a front of the wrist-worn device;
   a case back connected to the monitor case at a back of the wrist-worn device, the case back contacts a user's wrist when the wrist-worn device is worn by the user;
   a gearbox provided within the monitor case, the gearbox includes a magnetic coil, and is connected to the display;
   a crown dial exposed external to the monitor case and connected to the gearbox;
   monitor circuitry provided within the monitor case, at least in part, the monitor circuitry is configured to detect a heart rate of the user based on an EKG signal, where the case back is a first electrode of the monitor circuitry; and
   electrostatic discharge (ESD) protection circuitry connected between the case back and the gearbox, the ESD protection circuitry is configured to: (i) pass electrostatic charges in a path between: (a) the gearbox and the crown dial and (b) the case back, and (ii) isolate the case back from the gearbox.

2. The wrist-worn device of claim 1, wherein the ESD protection circuitry includes a diode which presents a high impedance path to the gearbox, between the gearbox and the case back.

3. The wrist-worn device of claim 1, wherein:
   the display includes at least one of an hour hand, a minute hand and a second hand of an analog watch;
   the gearbox is connected to the at least one of the hour hand, the minute hand and the second hand of the analog watch; and
   the crown dial can be manipulated by the user to adjust the at least one of the hour hand, the minute hand and the second hand of the analog watch.

4. The wrist-worn device of claim 1, further comprising a wrist band attached to the monitor case.

5. The wrist-worn device of claim 1, further comprising:
   a clamp which secures a battery;
   a second ESD protection circuitry connected between the clamp and the case back; and
   a second electrode of the monitor circuitry, the second electrode is exposed at a top or a side of the monitor case; wherein:
   the monitor circuitry includes a microcontroller; and
   the second electrode is a pushbutton of a switch, the switch connects the clamp and the microcontroller, to activate the monitor circuitry.

6. The wrist-worn device of claim 5, further comprising:
   a third electrode of the monitor circuitry, the third electrode is exposed at the top or a side of the monitor case; and
   a third ESD protection circuitry connected between the third electrode and the case back.

7. A device for monitoring a heart rate, comprising:
   a case;
   heart rate detection circuitry provided within the case, at least in part, and configured to determine heart rate information from an electrocardiogram signal;
   a gear assembly provided within the case and connectively coupled to the heart rate detection circuitry and a crown dial;
   a case back of the case, the case back is configured to sense a user biometric and is connected to the heart rate detection circuitry; and
   an electrostatic discharge (ESD) protection diode provided within the case and connected between the case back and the gear assembly, the ESD diode having an anode connected to the case back and a cathode connected to the gear assembly, wherein the ESD protection diode is configured to: (i) pass electro-static charges in a path between (a) the gear assembly and the crown dial and (b) the case back, and (ii) isolate the case back from the gear assembly.

8. The device of claim 7, wherein the gear assembly is connected to at least one of an hour hand, a minute hand and a second hand of an analog watch display.

9. The device of claim 7, further comprising:
an additional sensor positioned on the top face or side of the case, and connected to the heart rate detection circuitry; and
an additional ESD protection diode connecting the additional sensor and the case back.

10. The device of claim 7, further comprising:
two additional sensors connected to the heart rate detection circuitry, and externally exposed from the case, the two additional sensors and the case back are electrodes of the heart rate detection circuitry.

11. The device of claim 7, further comprising:
a module clamp connected to a battery, the module clamp and the battery are provided within the case; and
ESD protection circuitry connected between the module clamp and the case back.

12. A heart rate monitor, comprising:
a monitor case;
a display having both analog and digital components;
a mechanism input for adjusting the display, the mechanism input is exposed external to the monitor case and can be manipulated by a user;
a case back attached to the monitor case and configured as a sensor for receiving biometric data from a user;
one or more secondary sensors for receiving additional biometric data from the user;
monitor circuitry for receiving signals from the case back and the one or more secondary sensors, determining heart rate information from the signals, and providing the heart rate information to the display; and
ESD protection circuitry connecting the case back to mechanism input, the ESD protection circuitry protects the monitor circuitry from a voltage discharge.

13. The heart rate monitor of claim 12, wherein said one or more secondary sensors include:
at least one side push button sensor; and
at least one top mounted sensor.

14. The heart rate monitor of claim 12, wherein:
said heart rate monitor is a wrist worn monitor for detecting a pulse from a user's EKG signals; and
the ESD protection circuitry is configured to discharge an electro-static discharge voltage via the mechanism input and the case back, thereby protecting the monitor circuitry.

15. The wrist-worn device of claim 1, wherein:
the display includes at least one of an hour hand, a minute hand and a second hand of an analog watch; and
the gearbox is connected to the at least one of the hour hand, the minute hand and the second hand of the analog watch.

16. The wrist-worn device of claim 1, further comprising:
a second electrode of the monitor circuitry, the second electrode is exposed at the top or a side of the monitor case;
wherein the second electrode is a pushbutton for activating the monitor circuitry, causing a heart rate of the user to be displayed on the display.

17. The wrist-worn device of claim 1, further comprising:
a second electrode of the monitor circuitry, the second electrode is exposed at the top or a side of the monitor case;
wherein the monitor circuitry includes a differential amplifier which receives signals from the case back and the second electrode.

18. The wrist-worn device of claim 2, wherein:
an anode of the diode is connected to the case back and a cathode of the diode is connected to the gearbox.

19. The wrist-worn device of claim 1, wherein:
the ESD protection circuitry prevents electrical noise produced from the gearbox from reaching the monitor circuitry via the case back.

20. The wrist-worn device of claim 19, further comprising:
a module provided within the monitor case which provides a signal to the gearbox to drive the gearbox, where the gearbox produces the electrical noise when driven.

21. A wrist-worn device, comprising:
a monitor case;
a display connected to the monitor case at a front of the wrist-worn device;
a clamp provided within the monitor case, the clamp secures a battery;
monitor circuitry provided within the monitor case, at least in part, the monitor circuitry includes a microcontroller and is configured to detect a heart rate of a user based on an EKG signal;
a case back connected to the monitor case at a back of the wrist-worn device, the case back contacts a user's wrist when the wrist-worn device is worn by the user and is a first electrode of the monitor circuitry;
a pushbutton of a switch, the switch connects the clamp and the microcontroller, to activate the monitor circuitry to cause a heart rate of the user to be displayed on the display, when the pushbutton is pushed by the user;
the pushbutton is a second electrode of the monitor circuitry, and is exposed at a side of the monitor case; and
electrostatic discharge (ESD) protection circuitry which connects the clamp and the case back, the ESD is configured to pass electro-static charges in a path which includes the pushbutton, the clamp and the case back.

22. The wrist-worn device of claim 21, wherein:
the monitor circuitry includes a circuit board; and
the clamp includes an extension near an edge of the circuit board, between the edge and the pushbutton, where the pushbutton, when pushed, closes the switch by causing the extension to contact the edge.

* * * * *